(12) United States Patent
Maxson et al.

(10) Patent No.: US 12,239,348 B2
(45) Date of Patent: Mar. 4, 2025

(54) FRACTURE AND NONUNION RIB IMPLANTS

(71) Applicant: Zimmer Biomet CMF and Thoracic, LLC, Jacksonville, FL (US)

(72) Inventors: William Maxson, Ponte Vedra, FL (US); Brian Hatcher, Warsaw, IN (US)

(73) Assignee: Zimmer Biomet CMF and Thoracic, LLC, Jacksonville, FL (US)

( * ) Notice: Subject to any disclaimer, the term of this patent is extended or adjusted under 35 U.S.C. 154(b) by 1054 days.

(21) Appl. No.: 17/176,925

(22) Filed: Feb. 16, 2021

(65) Prior Publication Data

US 2021/0177474 A1    Jun. 17, 2021

Related U.S. Application Data

(63) Continuation of application No. 16/425,539, filed on May 29, 2019, now abandoned.

(Continued)

(51) Int. Cl.
*A61B 17/80*    (2006.01)
*A61B 17/86*    (2006.01)
(Continued)

(52) U.S. Cl.
CPC .......... *A61B 17/8076* (2013.01); *A61B 17/86* (2013.01); *A61F 2/28* (2013.01);
(Continued)

(58) Field of Classification Search
CPC .............................. A61F 2/28; A61B 17/8076
See application file for complete search history.

(56) References Cited

U.S. PATENT DOCUMENTS 3,710,789 A  *  1/1973  Ersek ................. A61B 17/8085
                                                            606/907
5,282,861 A     2/1994  Kaplan
(Continued)

FOREIGN PATENT DOCUMENTS

RU           2199288 C1     2/2003
WO      WO-2019232058 A1   12/2019

OTHER PUBLICATIONS

"International Application Serial No. PCT/US2019/034407, International Preliminary Report on Patentability mailed Dec. 10, 2020", 9 pgs.

(Continued)

*Primary Examiner* — Christopher D. Prone
(74) *Attorney, Agent, or Firm* — SCHWEGMAN LUNDBERG & WOESSNER, P.A.

(57) ABSTRACT

A rib implant securable to first and second rib portions of a rib. The rib implant can include a body, a first porous stem, and a second porous stem. The body can be configured to span a first rib portion of a rib and a second rib portion of the rib. The first porous stem can extend from the body and the first porous stem can be insertable into a first intramedullary canal of the first rib portion. The second porous stem can extend from the body opposite the first porous stem. The second porous stem can be insertable into a second intramedullary canal of the second rib portion to, together with the first porous stem, secure the first rib portion and the second rib portion.

11 Claims, 10 Drawing Sheets

Related U.S. Application Data

(60) Provisional application No. 62/679,147, filed on Jun. 1, 2018.

(51) Int. Cl.
 *A61F 2/28* (2006.01)
 *A61B 17/00* (2006.01)
 *A61F 2/30* (2006.01)

(52) U.S. Cl.
 CPC ............... *A61B 2017/00004* (2013.01); *A61F 2002/30062* (2013.01); *A61F 2002/30224* (2013.01); *A61F 2002/30784* (2013.01); *A61F 2002/3093* (2013.01)

(56) References Cited

U.S. PATENT DOCUMENTS

| | | |
|---|---|---|
| 8,920,512 B2 | 12/2014 | Maxson et al. |
| 2003/0073999 A1 | 4/2003 | Putnam |
| 2005/0216082 A1 | 9/2005 | Wilson et al. |
| 2010/0094294 A1 | 4/2010 | Gillard et al. |
| 2012/0296440 A1 | 11/2012 | Choux et al. |
| 2012/0296441 A1* | 11/2012 | Mikhail ................ A61F 2/2803 623/23.63 |
| 2014/0088654 A1 | 3/2014 | Marasco |
| 2015/0196396 A1 | 7/2015 | Thomas |
| 2016/0030088 A1 | 2/2016 | Lim et al. |
| 2016/0058484 A1 | 3/2016 | Mccombs-Stearnes et al. |
| 2017/0156766 A1 | 6/2017 | Anderson et al. |
| 2019/0365440 A1 | 12/2019 | Maxson et al. |

OTHER PUBLICATIONS

"International Application Serial No. PCT/US2019/034407, International Search Report mailed Aug. 22, 2019", 6 pgs.

"International Application Serial No. PCT/US2019/034407, Written Opinion mailed Aug. 22, 2019", 9 pgs.

* cited by examiner

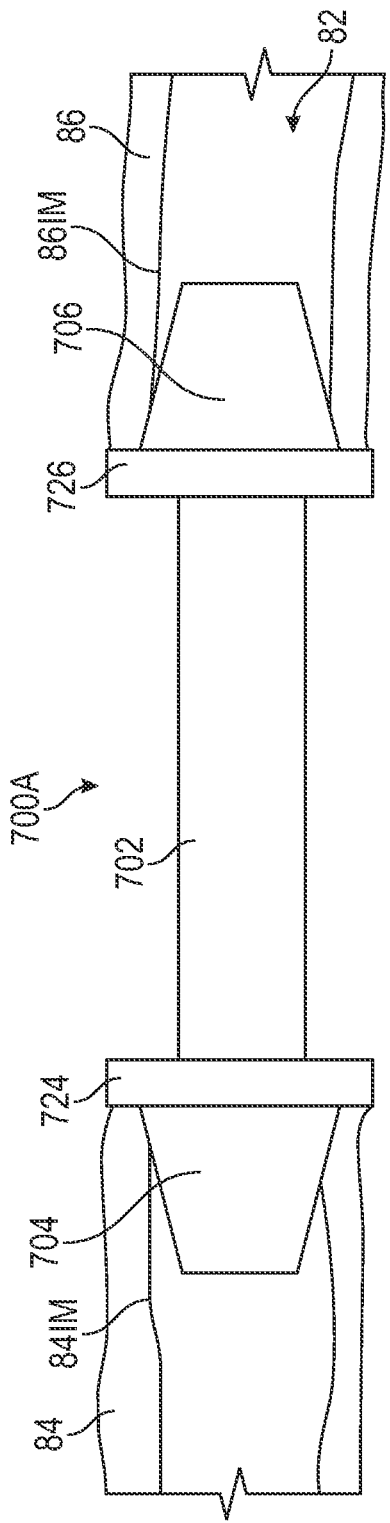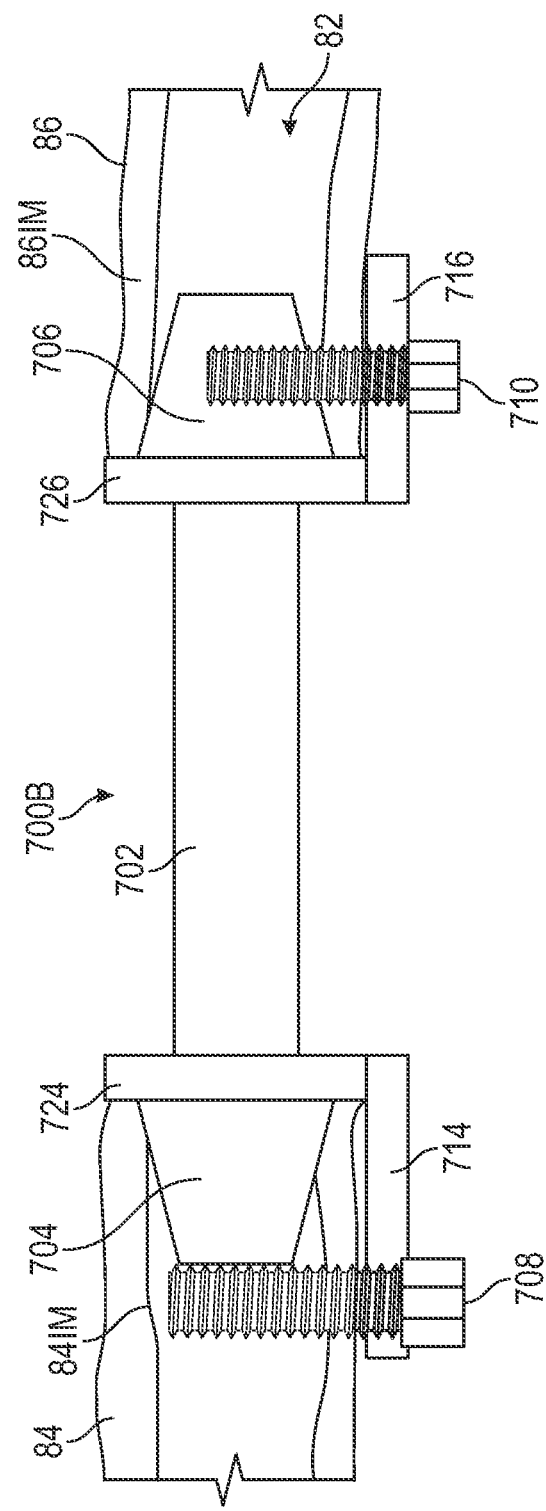

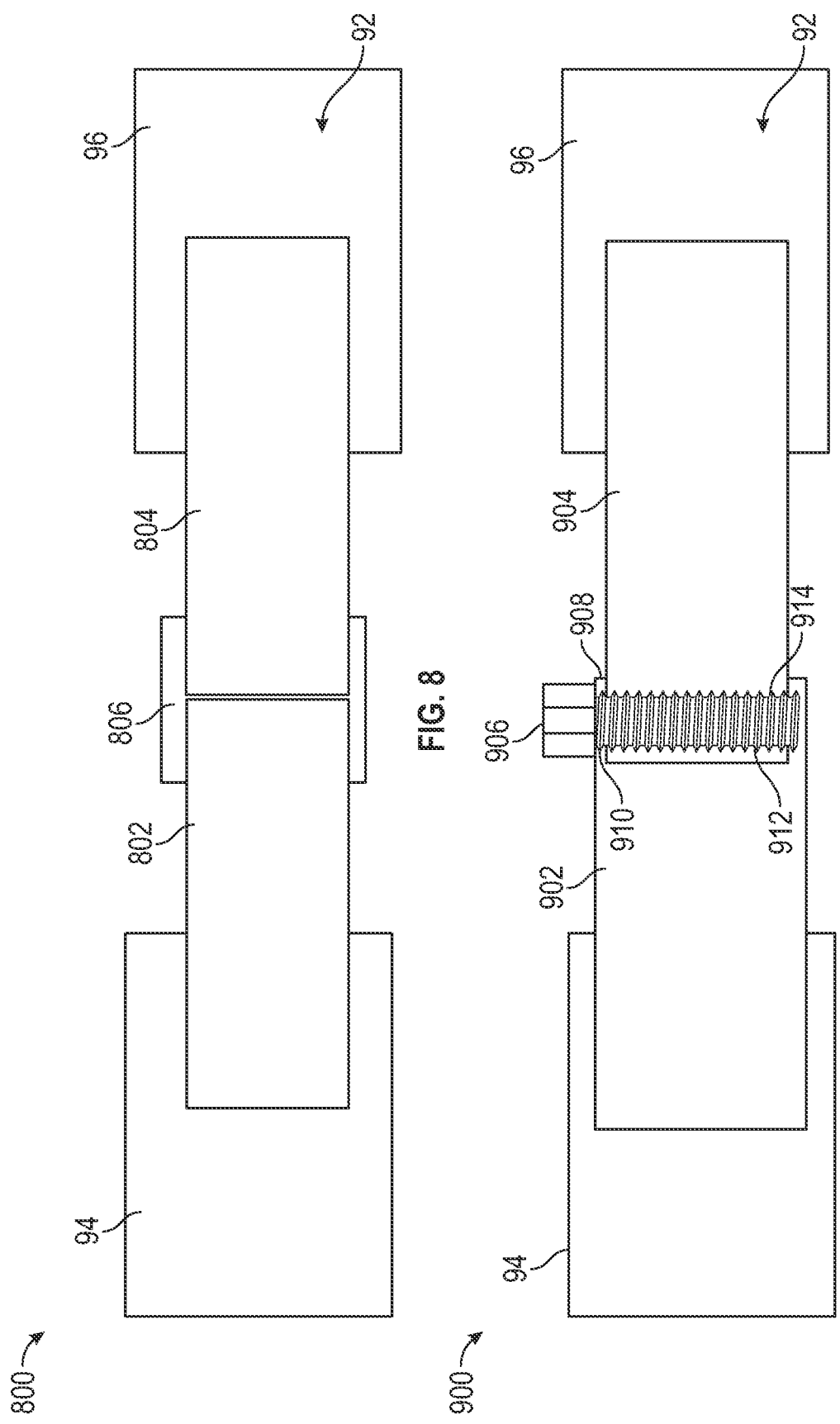

FRACTURE AND NONUNION RIB IMPLANTS

CLAIM OF PRIORITY

This application is a continuation of U.S. application Ser. No. 16/425,539, filed May 29, 2019, which claims the benefit of U.S. Provisional Patent Application Ser. No. 62/679,147, filed on Jun. 1, 2018, the benefit of priority of each of which is claimed hereby, and each of which is incorporated by reference herein in their entireties.

BACKGROUND

The present invention relates generally to apparatus and systems for rib implants. For patients with various rib injuries, surgeons sometimes install a plate to secure fractured rib portions to each other. In some cases, a nonunion of the rib sections may occur due to damaged rib portions or improper healing. In these cases, a portion of the rib may need to be removed. To regain anatomical integrity between the rib segments and to protect organs directly behind the ribcage, surgeons use donor tissue and/or plates and screws to bridge the void and to fasten the rib segments to each other.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 7A illustrates an isometric view of a rib implant secured to a rib, in accordance with at least one example of this disclosure.

FIG. 7B illustrates an isometric view of a rib implant secured to a rib, in accordance with at least one example of this disclosure.

FIG. 8 illustrates an isometric view of a rib implant secured to a rib, in accordance with at least one example of this disclosure.

FIG. 9 illustrates an isometric view of a rib implant secured to a rib, in accordance with at least one example of this disclosure.

DETAILED DESCRIPTION

In some cases of a broken rib, surgeons use plates and screws to bridge the fracture and to secure rib segments to each other. However, these plates and fasteners can be palpable to a patient and in some cases may be prone to catching on nearby soft tissues, causing further discomfort.

This disclosure provides a solution to these issues through use of an implant that includes stems and a body that are insertable into an intramedullary canal of the ribs. An implant that is insertable into the intramedullary canal can help reduce palpability. Further, the implant can include one or more components made of porous material configured to promote bone ingrowth with can help effect fixation of the implant to the ribs.

In some other cases, a nonunion of rib sections may occur due to damaged rib portions or improper healing. In these cases, a portion of the rib may require removal. To regain anatomical integrity between the rib segments and to protect organs directly behind the ribcage, surgeons can use donor bones from a cadaver or donor bone from the patient (such as from the patient's femur). In some of these cases, surgeons may use plates and screws to bridge the void and to fasten the rib segments and donor materials to each other. However, these plates and fasteners can be palpable to a patient and can in some cases catch on nearby soft tissues causing further discomfort. Also, a gap may remain when plates are used to bridge the gap. Further, when patients require use of donor bone material from themselves, there may be associated pain and suffering. For example, a patient may donate femoral bone for a rib fracture repair.

This disclosure provides a solution to these issues through use of an implant that includes a body configured to provide a substantially natural transition between resected rib sections. The implant can also include one or more components made of porous material configured to promote bone ingrowth which can help effect fixation of the implant to the ribs. The implant can further include plates, flanges, and fasteners to further secure the implant to the rib portions.

As used herein, the terms "proximal" and "distal" should be given their generally understood anatomical interpretation. The term "proximal" refers to a direction generally toward the torso of a patient or base or handle of a tool, and "distal" refers to the opposite direction of proximal, i.e., away from the torso of a patient or toward the working end of the tool.

Figure 1:
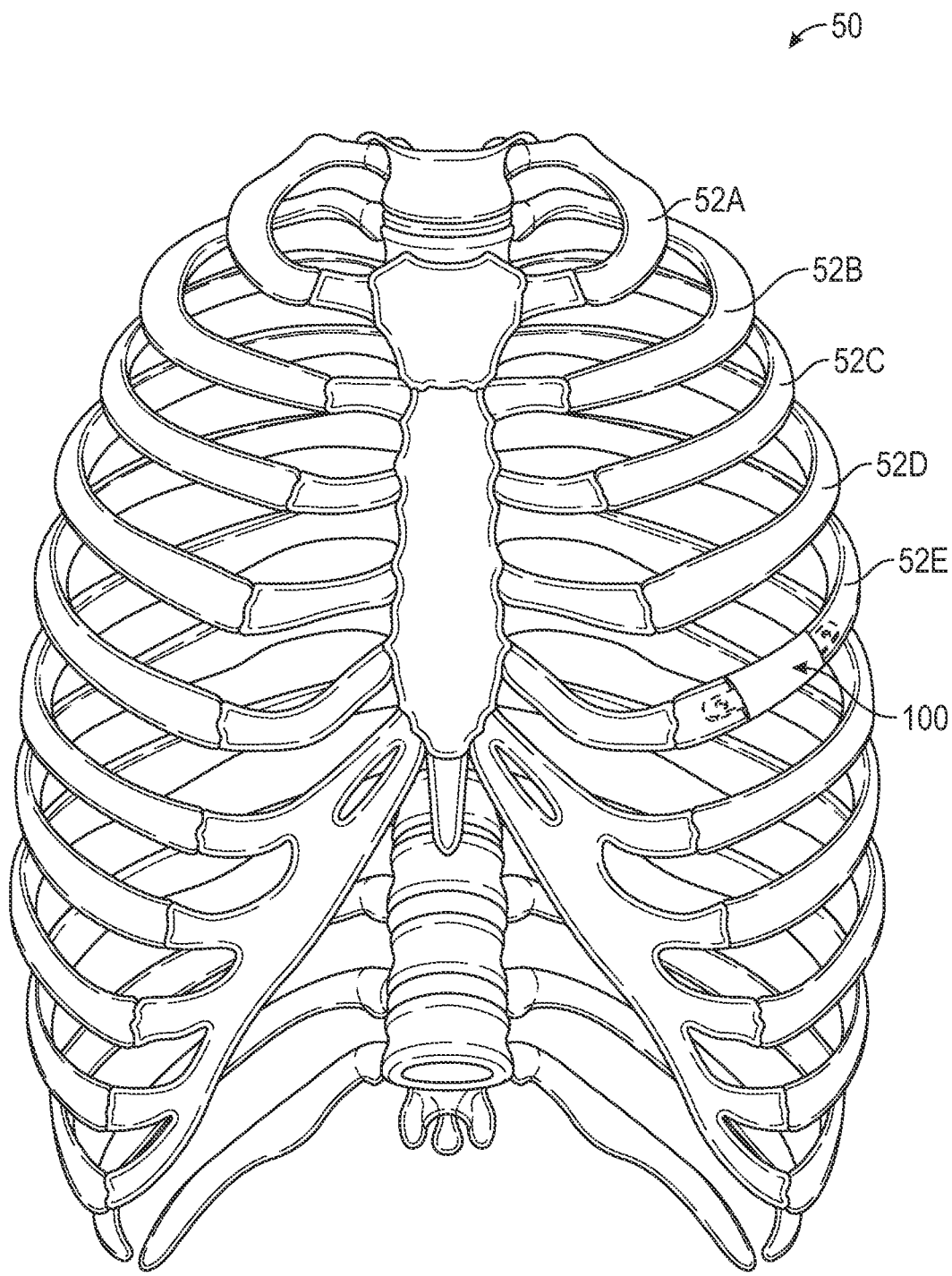
FIG. 1 shows an isometric view of a rib implant coupled to a rib cage of a patient, in accordance with an example of the present disclosure.

FIG. 1 shows an isometric view of a rib implant coupled to a rib cage of a patient, in accordance with an example of the present disclosure. FIG. 1 shows rib cage 50 including ribs 52A-52E and implant 100. In some examples, rib cage 50 can be a rib cage of a human, such as a patient, where rib 52E can be a fractured rib of rib cage 50. In this example, rib implant 100 can be secured to adjacent ends of rib 52E, which may be fractured and/or resected. Once secured to adjacent ends of rib 52E, rib implant 100 can provide a bridge between rib portions. Further details of rib implant 100 are discussed below with respect to FIG. 2.

Figure 2:
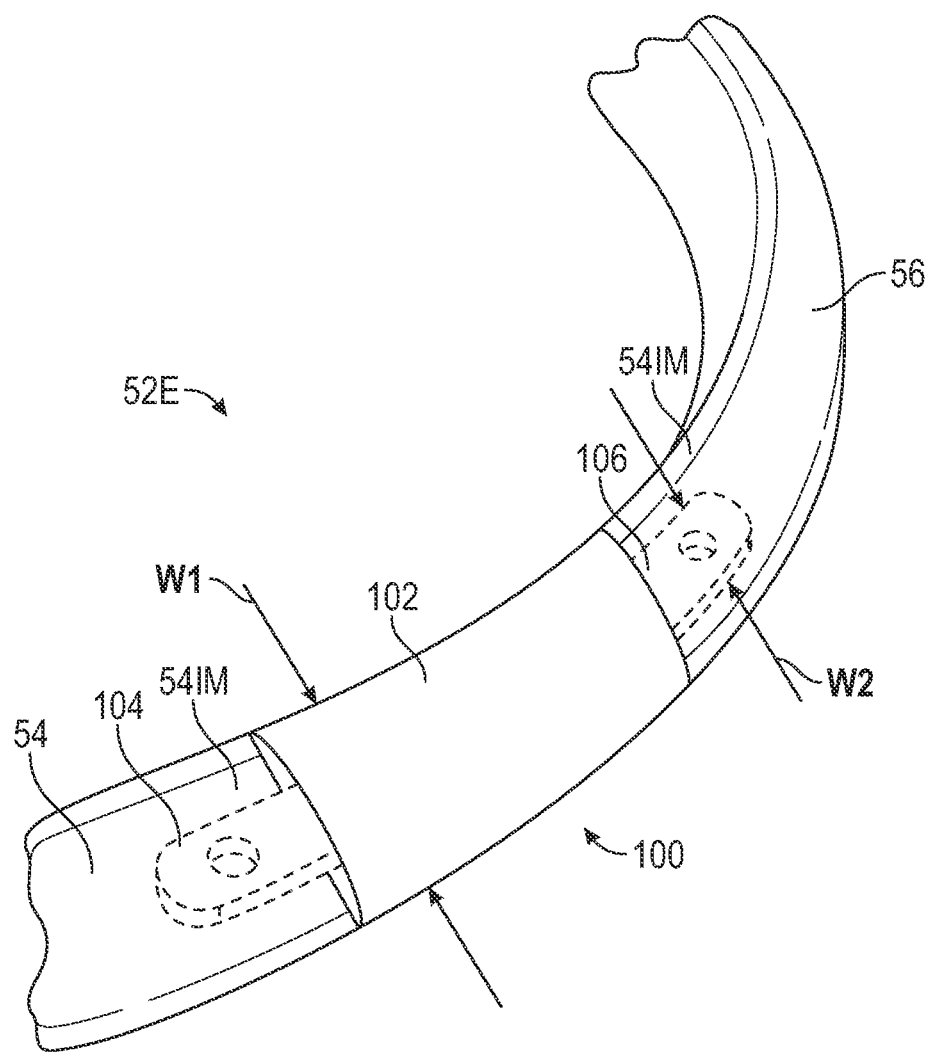
FIG. 2 illustrates an isometric view of a rib implant secured to a rib, in accordance with at least one example of this disclosure.

FIG. 2 illustrates an isometric view of rib implant 100 secured to rib 52E, in accordance with at least one example of this disclosure. Rib implant 100 can include body 102, medial stem 104, and lateral stem 106. Also shown in FIG. 2 is rib 52E, which can include medial end 54 and lateral end 56. Medial end 54 can include intramedullary canal 54IM and medial end 56 can include intramedullary canal 56IM. Also shown in FIG. 2 are widths W1 and W2 and orientation indicators Medial and Lateral.

Rib implant 100 can be a rigid or semi-rigid member made of a single piece (or multiple pieces in some examples). Rib implant 100 can be made of solid biocompatible materials such as stainless steels, cobalt chromium, titanium, combinations thereof, or the like. In some examples, portions of rib implant 100 can be made of porous or semi-porous materials configured to promote bone ingrowth to enhance fixation (such as through osseointegration) of implant 100 to rib 52E.

One porous material that can be used is OsseoTi™ porous metal from Zimmer Biomet™ (Warsaw, Ind.). OsseoTi can be made of Ti6Al4V and can have a porous structure that generally mimics a porous structure of human cancellous bone. Also, the porous material can be Trabecular Metal™, also from Zimmer Biomet. Such a material may be formed from a reticulated vitreous carbon foam substrate that can be infiltrated and coated with a biocompatible metal, such as tantalum, such as using a chemical vapor deposition ("CVD") process in the manner disclosed in detail in U.S. Pat. No. 5,282,861. Also, the porous material can be Regenerex®, also from Zimmer Biomet. In other examples, other porous materials can be used.

Body 102 can be a rigid or semi-rigid member and can be sized to bridge medial end 54 and lateral end 56 of rib 52E. In this example, body 102 can be sized to replace a portion of rib 52E, such that body 102 abuts each of ends 54 and 56, as shown in FIG. 2. In some examples, body 102 can be sized and shaped to match a size and a shape of each of rib portion 54 and rib portion 56 to create a substantially uniform bridge between the first end and the second end. In other examples, body 102 can be sized to be inserted into an intramedullary canal of rib 52E, as discussed below with respect to FIGS. 3A-3C.

Medial stem 104 can be a portion of rib implant 100 extending medially from a medial face of body 102. Similarly, lateral stem 106 can be a portion of rib implant 100 extending laterally from a lateral face of body 102. In some examples, medial stem 104 and lateral stem 106 can be of various sizes. In the example of FIG. 2, medial stem 104 and lateral stem 106 can have a width that is smaller than a width W2, which can be smaller than a width W1 of body 102. This can allow medial stem 104 to be insertable into intramedullary canal 54IM and can allow lateral stem 106 to be insertable into intramedullary canal 56IM, as shown in FIG. 2. In other examples, body 102 can have a width similar to that of W2 so that body 102 can be inserted into both intramedullary canal 54IM and intramedullary canal 56IM.

In some examples, one or more of medial stem 104 and lateral stem 106 can include one or more barbs, or sharp directional projections, configured not to limit insertion of the stems into the intramedullary canals, and configured to engage the bone to help prevent back-out the stem from the rib portions. For example, a barb on medial stem 104 can help prevent back-out of medial stem 104 from rib portion 54.

In some examples, one or more of medial stem 104 and lateral stem 106 can have consistent dimensions throughout a medial-to-lateral length of each of the medial stem 104 and lateral stem 106, respectively. For example, when each of medial stem 104 and lateral stem 106 are substantially oval in geometric shape, each of medial stem 104 and lateral stem 106 can have a consistent width and height throughout the length. In other examples, either of of medial stem 104 and lateral stem 106 can be tapered throughout the medial-to-lateral length to help make insertion into intramedullary canal 54IM easier and to help ensure that each of medial stem 104 and lateral stem 106 can engage the bone of respective rib portions 54 and 56.

In this example, body 102 can be made of solid biocompatible materials such as stainless steels, cobalt chromium, titanium, combinations thereof, or the like. Also, medial stem 104 and lateral stem 106 can each be made of, or coated with, porous or semi-porous materials configured to promote bone ingrowth to enhance fixation (such as through osseointegration), such as Trabecular Metal™, Regenerex®, or OsseoTi®, described above. In other examples, other porous materials can be used.

In operation of some examples, rib 52E can be prepared to receive implant 100. Preparations can include resecting rib 52E, as discussed further below. When rib 52E is ready to receive implant 100, medial stem 104 can be inserted into intramedullary canal 54IM of rib portion 54 until a medial face of body 102 abuts a lateral face of rib portion 54. In some examples, width w1 can be sized to be substantially the same size as rib portions 54 and 56 to help limit translation of medial stem 104 and lateral stem 106 into respective intramedullary canals. Body 102 can help reduce palpability of implant 100 and catching of implant 100 on nearby soft tissues, by having width W1 that is of similar size to rib portions 54 and 56.

Once medial stem 104 is fully inserted into intramedullary canal 54IM, lateral stem 106 can be inserted into intramedullary canal 56IM until a lateral face of body 102 contacts a medial face of rib portion 56, limiting translation of lateral stem 106 into intramedullary canal 56IM and ensuring insertion of stem 104 into intramedullary canal 54IM. In some examples, each of medial stem 104 and lateral stem 106 can engage each of intramedullary canal 54IM and intramedullary canal 56IM, respectively, in a press-fit (or interference fit) engagement. In these examples, width W2 of each of medial stem 104 and lateral stem 106 can be sized to promote the press-fit engagement to secure implant 100 to rib portions 54 and 56 to provide support for rib 52E.

After both of medial stem 104 and lateral stem 106 are secured within respective intramedullary canals, the procedure can be completed. Following the procedure, each of medial stem 104 and lateral stem 106, being made of a porous material, can promote bone ingrowth from respective rib portions into medial stem 104 and lateral stem 106 to further secure medial stem 104 and lateral stem 106 to rib portions 54 and 56, respectively. Because body 102 can be of a non-porous material, body 102 can help limit ingrowth of soft tissues into body 102, to help increase patient comfort of implant 100.

In other examples, each of medial stem 104 and lateral stem 106 can engage each of intramedullary canal 54IM and intramedullary canal 56IM in other configurations, as discussed further in the examples below. Though installation of implant 100 is described above using the example of installing medial stem 104 first, lateral stem 106 can be installed first in some examples. In other examples, medial stem 104 and lateral stem 106 can be inserted simultaneously, such as when rib 52E is a floating rib.

Figure 3A:
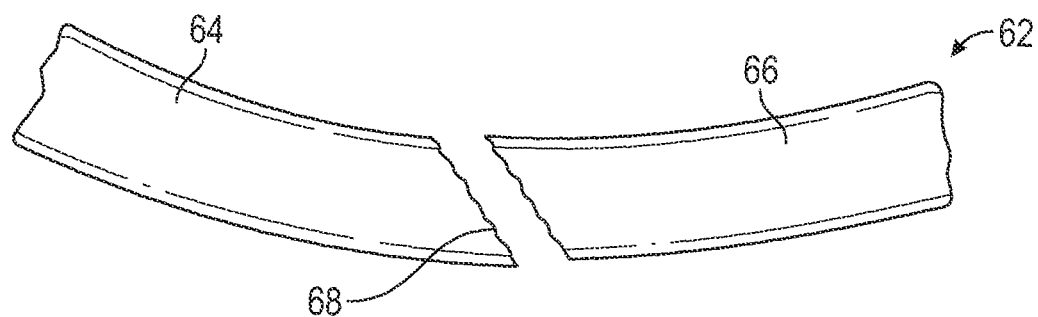
FIG. 3A illustrates an isometric view of a fractured rib, in accordance with at least one example of this disclosure.
Figure 3B:
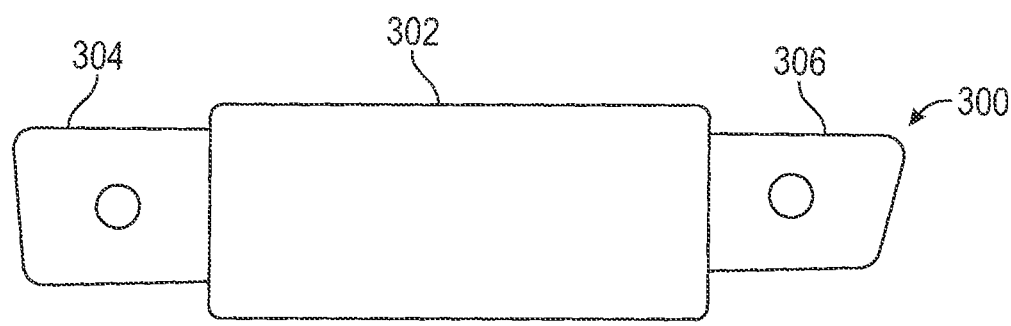
FIG. 3B illustrates an isometric view of a rib implant, in accordance with at least one example of this disclosure.
Figure 3C:
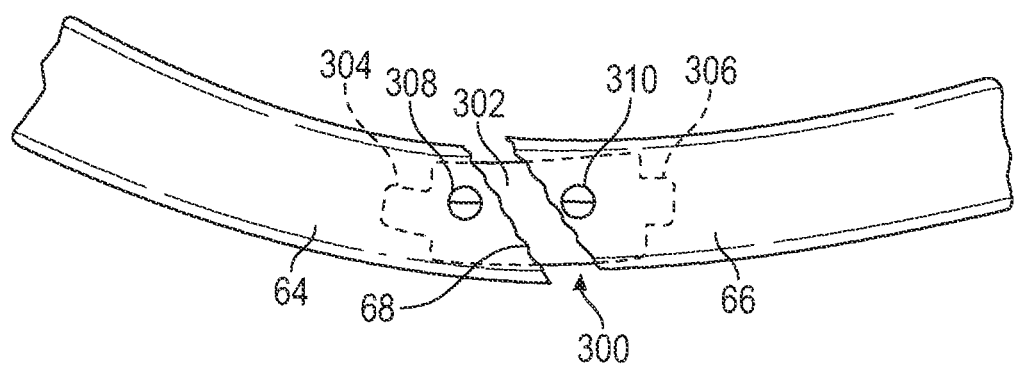
FIG. 3C illustrates an isometric view of a rib implant secured to a rib, in accordance with at least one example of this disclosure.

FIG. 3A illustrates an isometric view of fractured rib 62, in accordance with at least one example of this disclosure. FIG. 3B illustrates an isometric view of rib implant 300, in accordance with at least one example of this disclosure. FIG. 3C illustrates an isometric view of a rib implant secured to a rib, in accordance with at least one example of this disclosure. FIGS. 3A-3C are discussed together below.

FIGS. 3A-3C show an example of a procedure of installing rib implant 300 in rib 62. In some examples, implant 300 can be a splint configured to help fill a void between rib portions 64 and 66. The previously discussed implants may be used in similar procedures. FIG. 3A shows rib 62, which can include ends 64 and 66 with fracture 68 separating portions 64 and 66. FIGS. 3B and 3C show implant 300, which can include body 302, medial stem 304, lateral stem 306, and fasteners 308 and 310. Also shown in FIGS. 3A-3C are orientation indicators Medial and Lateral.

In the example of FIGS. 3A-3C, implant 300 can be similar to implant 100 described above with respect to FIGS. 1 and 2, except that body 302 can be sized to have a width such that body 302 can be insertable into intramedullary canals of rib portions 64 and 66. As shown in FIG. 3C, body 302 can be fully inserted into intramedullary canals of rib portions 64 and 66 to create a splint between rib portions 64 and 66. In this example, each of medial stem 304 and lateral stem 306 are also inserted into rib portions 64 and 66 and can made of porous materials, such as those described above with respect to FIGS. 1 and 2.

Body 302 can be made of either porous or non-porous materials. For example, body 302 can be made a porous or semi-porous material, such as Trabecular Metal™, Regenerex®, or OsseoTi®, described above. In some examples, body 302 can be non-porous, as described above with respect to FIGS. 1 and 2 to help limit soft tissue attachment and to help reduce friction during insertion. In some examples, implant 300 can be made of a resorbable material, or a material configured to be absorbed by the body over time. In one example, the resorbable material can be Lactosorb® of Zimmer Biomet™ (Warsaw, Ind.).

In other examples, for example when a gap between rib portions 64 and 66 (fracture 68) is a small gap and when soft tissue attachment may be less of a concern, body 302 can be a made of a porous material, to help promote bone ingrowth into body 302 and implant 300 to help secure implant 300 to rib 62.

In some examples, body 302 can be of the same width and height as medial stem 304 and lateral stem 306, such that implant 300 (or the splint) can be of a consistent shape and size throughout an entire medial-to-lateral length of implant 300.

In some examples, as shown in FIG. 3C, fasteners 308 and 310 can be screws, bolts, rivets, or the like, configured to engage rib portions 64 and/or 66 and implant 300. In one example, fastener 308 can engage rib portion 64 and body 302 and fastener 310 can engage rib portion 66 and body 302 to secure rib portions 64 and 66 to body 302. In this way, fasteners 308 and 310 can help limit movement of implant 300 relative to rib portions 64 and 66. Though FIG. 3C shows two of fasteners 308 and 310, fewer fasteners, such as only fastener 308 or 310 can be used in some examples. In other examples, more fasteners can be used, such as 3, 4, 5, 6, 7, 8, 9, 10, or the like. In some example, pilot holes through rib portions 64 and/or 66 can be used and in other examples, pilot holes may not be used. Similarly, bores or holes in body 302 may or may not be used to receive fasteners 308 and 310.

Figure 4A:
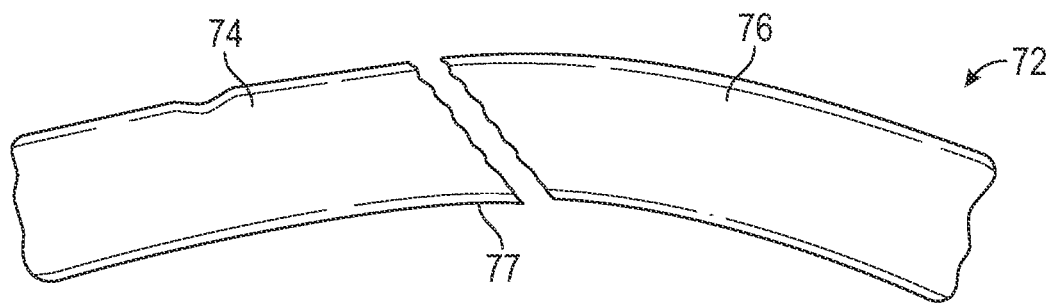
FIG. 4A illustrates an isometric view of a fractured rib, in accordance with at least one example of this disclosure.
Figure 4B:
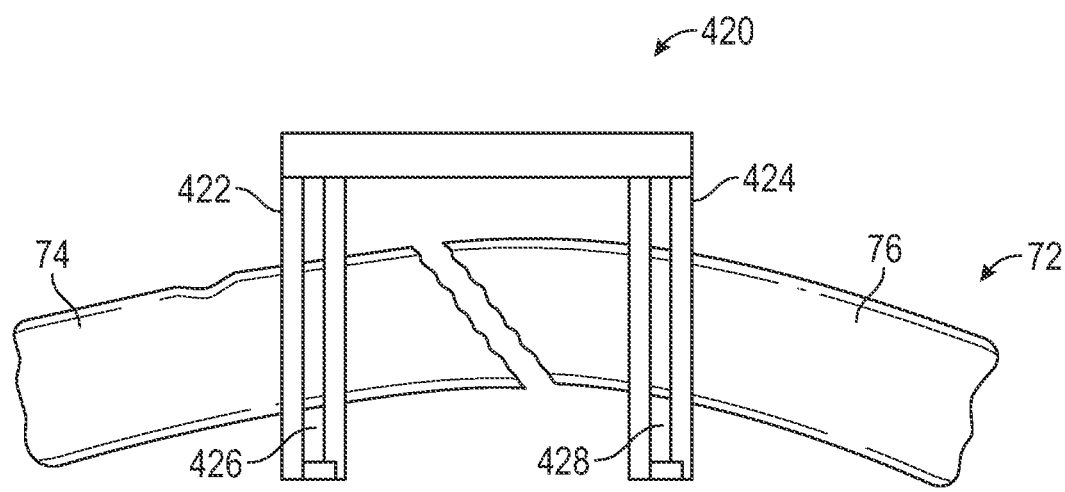
FIG. 4B illustrates an isometric view of a fractured rib and a cut guide, in accordance with at least one example of this disclosure.
Figure 4C:
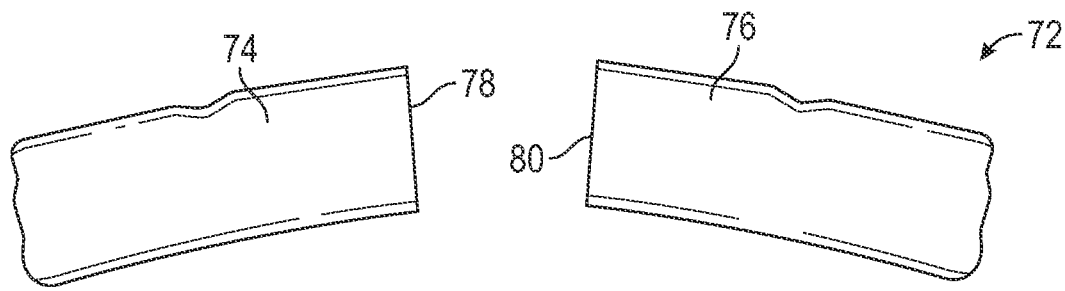
FIG. 4C illustrates an isometric view of a resected rib, in accordance with at least one example of this disclosure.
Figure 4D:
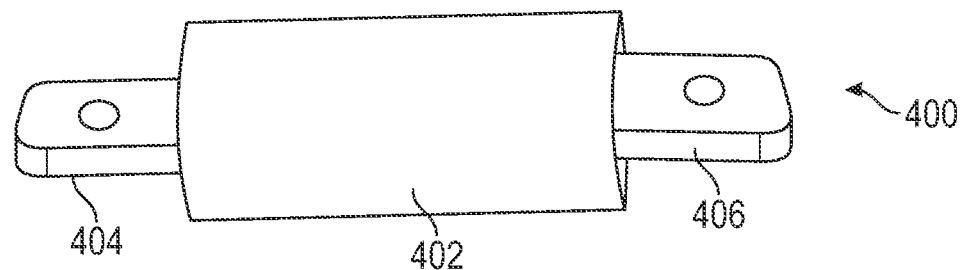
FIG. 4D illustrates an isometric view of a rib implant, in accordance with at least one example of this disclosure.
Figure 4E:
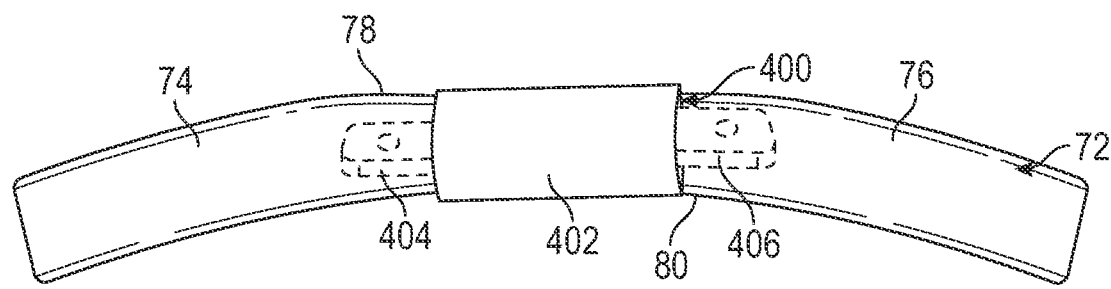
FIG. 4E illustrates an isometric view of a rib implant secured to a rib, in accordance with at least one example of this disclosure.
Figure 4F:
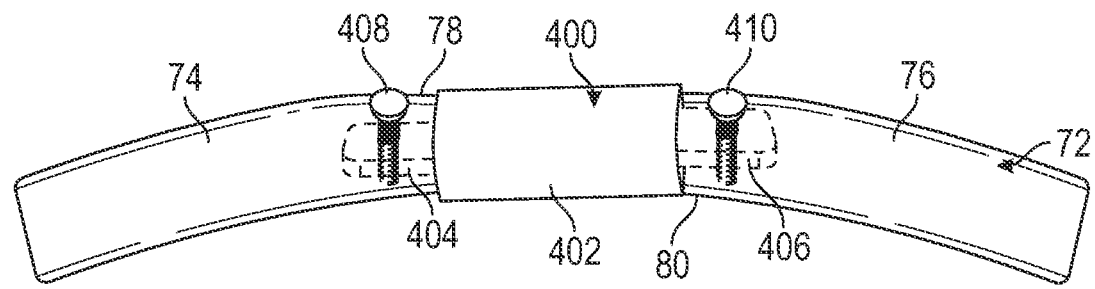
FIG. 4F illustrates an isometric view of a rib implant fastened to a rib, in accordance with at least one example of this disclosure.

FIG. 4A illustrates an isometric view of rib 72, in accordance with at least one example of this disclosure. FIG. 4B illustrates an isometric view of fractured rib 72 and cut guide 420, in accordance with at least one example of this disclosure. FIG. 4C illustrates an isometric view of resected rib 72, in accordance with at least one example of this disclosure. FIG. 4D illustrates an isometric view of rib implant 400, in accordance with at least one example of this disclosure. FIG. 4E illustrates an isometric view of rib implant 400 secured to rib 72, in accordance with at least one example of this disclosure. FIG. 4F illustrates an isometric view of rib implant 400 fastened to rib 72, in accordance with at least one example of this disclosure.

FIGS. 4A-4E show an example of a procedure of installing rib implant 400 in rib 72. Any of the previously discussed implants may be used in similar procedures. FIGS. 4A-4C, 4E, and 4F show rib 72, which can include rib portions 74 and 76 separated by fracture 77 (FIGS. 4A and 4B). Rib portion 74 can include resected end 78 and rib portion 76 can include resected end 80 (FIGS. 4C, 4E, and 4F). Cut guide 420 (shown in FIG. 4B) can be a part of a system including implant 400, where cut guide 420 can include guides 422 (including slot 426) and 424 (including slot 428). Implant 400 (shown in FIGS. 4D-4F) can include body 402, medial stem 404, and lateral stem 406.

As shown in FIG. 4A, rib 72, which can be a rib of a patient, can have fracture 77 separating ends 74 and 76. As shown in FIG. 4B, cut guide 420 can be positioned relative to rib 72, for example, such that guide 422 is on a medial side of fracture 77 (aligned with a portion of rib portion 74) and guide 424 is on a lateral side of fracture 77 (aligned with a portion of rib portion 76). In some examples, when cut guide 420 is in a desired position, a blade or saw can be passed through opening 426 of guide 422 to resect rib portion 74 at a desired location. Similarly, the blade or saw can be passed through opening 428 of guide 424 to resect rib portion 76 at a desired location. After resection, rib portion 74 can have resected end 78 and rib portion 76 can have resected end 80. In some examples, guides 422 and 424 can be sized and shaped to create resected ends 78 and 80, respectively, so that resected ends 78 and 80 are better suited to receive implant 400.

Implant 400 can be similar to implant 100 described above with respect to FIGS. 1-2, such that body 402 can be sized to have a width configured to engage resected ends 78 and 80, respectively, of rib portions 74 and 76. In some examples, substantially matching the width of body 402 to rib portions 74 and 76 (for example, by using cut guide 420 and/or by providing body 402 with a desired width) can help provide a relatively consistent profile across rib portion 74, body 402, and rib portion 76, to help reduce palpability and to help provide a natural feel to a patient to help increase patient comfort.

As shown in FIGS. 4E and 4F, each of medial stem 404 and lateral stem 406 can be inserted into rib portions 74 and 76 and can made of porous materials, such as those described above with respect to stems 104 and 106 of FIGS. 1 and 2, to help promote bone ingrowth. In some examples, body 402 can be made of either porous or non-porous materials. In this example, body 402 can be non-porous, as described above with respect to FIGS. 1 and 2, to help limit soft tissue attachment and to help reduce friction between body 402 and soft tissue.

Fasteners 408 and 410 are shown in FIG. 4F, which can be screws, bolts, rivets, or the like. Though two fasteners are shown, a single fastener can be used in other examples. For example, only fastener 408 can be used to secure rib portion 74 to medial stem 404. By keeping rib portion 76 free from lateral stem 406, relatively small movement may occur following installation, which can help healing and proper setting, in some examples. In other examples, where it is desired that implant 400 not move at all (or move very little), two or more fasteners can be used to secure each of medial stem 404 and lateral stem 406 to rib portions 74 and 76, respectively. In other examples, more than two fasteners can be used, such as 3, 4, 5, 6, 7, 8, 9, 10, or the like.

As shown in FIG. 4F, fastener 408 can be sized to pass through rib portion 74, through medial stem 404, and into a portion of rib portion 74 but not extending beyond rib portion 74 (remaining within rib portion 74). In other examples, fastener 408 can be sized to extend partially into medial stem 404. Fastener 410 can be sized similarly to fastener 408, in some examples.

Figure 5:
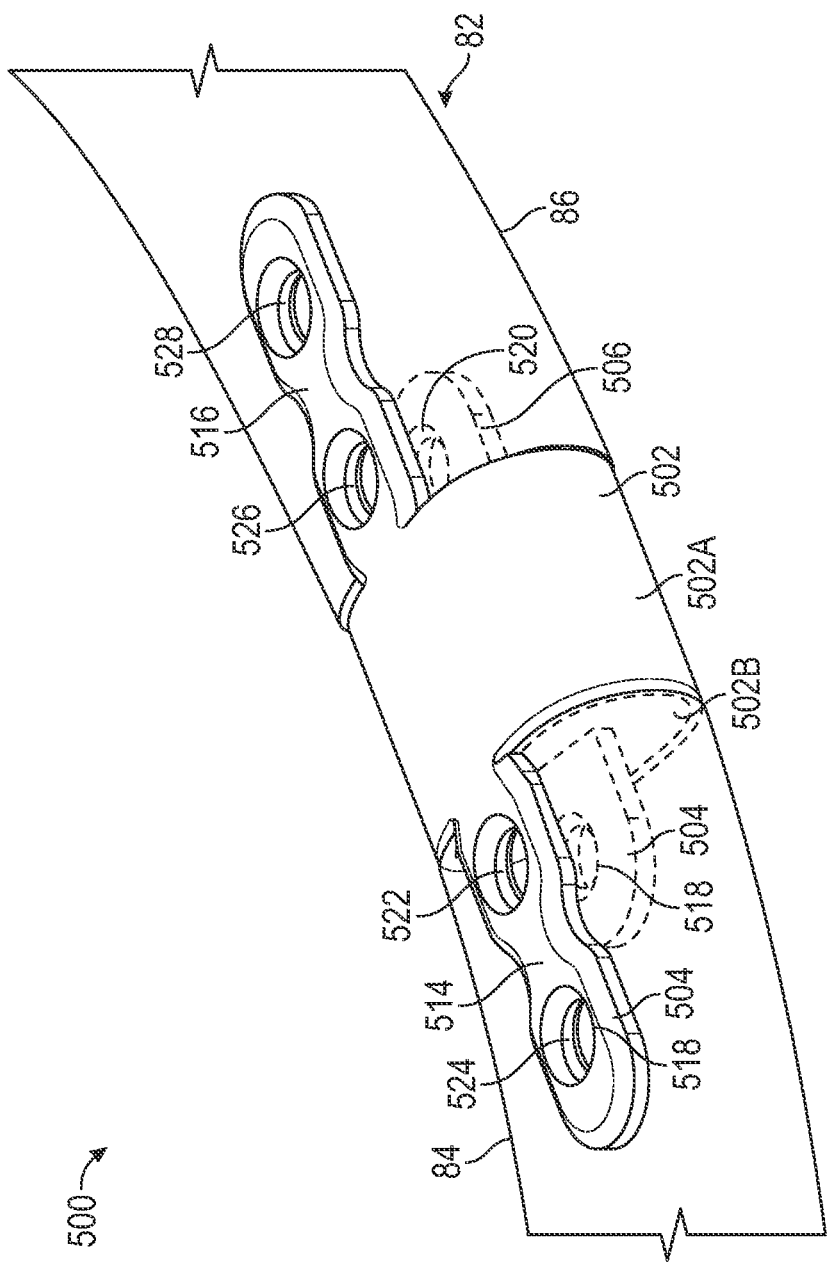
FIG. 5 illustrates an isometric view of a rib implant secured to a rib, in accordance with at least one example of this disclosure.

FIG. 5 illustrates an isometric view of rib implant 500 secured to rib 82, in accordance with at least one example of this disclosure. Rib implant 500 can include stems and can also include plates extending medially and laterally, where the plates engage an outer surface of the rib for affixing the implant to the rib using fasteners. Any of the previously discussed implants can be modified to include plates.

Rib implant 500 can include body 502, medial stem 504, lateral stem 506, medial plate 514, and lateral plate 516. Medial stem 504 can include stem bore 518 and lateral stem 506 can include stem bore 520. Medial plate 518 can include plate bores 522 and 524 and lateral plate 520 can include plate bores 526 and 528. Also shown in FIG. 5 is rib 82 (including rib portions 84 and 86) and orientation indicators Medial and Lateral.

Rib implant 500 can be similar to rib implants 100 and 400 discussed above in that body 502 can be sized to abut two resected ends of rib 82 to span rib portions 84 and 86, such as to create a substantially uniform section of rib 82. Rib implant 500 can differ, in one example, in that rib implant 500 can include medial plate 514 and lateral plate 516. Medial plate 514 can extend medially from outer portion 502A of body 502. In some examples, medial plate 514 can be substantially parallel to medial stem 504. Similarly, lateral plate 516 can extend laterally from outer portion 502A of body 502. In some examples, lateral plate 516 can be substantially parallel to lateral stem 506.

In some examples, one or more of medial plate 514 and lateral plate 516 can have a peanut-shape from a top perspective with respect to FIG. 5. That is, for example, a width of medial plate 514 can be smaller between bores 522 and 524. This reduced width can help allow for medial plate 514 to be bent or shaped to match a contour of rib portion 84. Lateral plate 516 can be optionally similarly configured.

Bores 518 and 520 of medial stem 504 and lateral stem 506, respectively, can be configured to receive a fastener (such as a screw, rivet, bolt, or the like) therethrough. Similarly, each of bores 522, 524, 526, and 528 can be configured to receive a fastener (such as a screw, rivet, bolt, or the like) therethrough. In some examples, bore 522 of medial plate 514 can be substantially aligned or coaxial with bore 518 of stem 504 such that bores 522 and 518 can receive a common fastener therethrough. Bores 526 of lateral plate 516 and 520 of lateral stem 506 can be similarly aligned to receive a common fastener. Also, bore 524 of medial plate 514 can receive a fastener therethrough and bore 528 of lateral plate 516 can receive a fastener therethrough. Though two bores of each of medial plate 514 and lateral plate 516 are shown, each of medial plate 514 and lateral plate 516 can include fewer bores, such as one each, or more bores, such as 3, 4, 5, 6, 7, 8, 9, 10, or the like.

In some examples, one or more of bores 522, 524, 526, and 528 can be threaded bores. In some examples, the threading of bores 522, 524, 526, and 528 can allow for each of bores 522, 524, 526, and 528 to receive locking fasteners (such as a locking screw or bolt) to secure to each of bores 522, 524, 526, and 528 to help prevent back-out of each fastener from medial stem 504, medial plate 514, lateral stem 506, and/or lateral plate 516.

Rib implant 500 can also differ in that body 502 can include an outer portion 502A and inner portion 502B. In some examples, outer portion 502A can be, for example, a non-porous biocompatible material, which can be selected to help prevent soft tissue adhesion and reduce friction between body 502 and soft tissues. Inner portion 502b can be comprised of a porous or semi-porous material, such as Trabecular Metal™, Regenerex®, or OsseoTi®, which can help promote bone ingrowth from rib portions 84 and 86 into inner portion 502B to enhance fixation (such as through osseointegration). In this way, body 502 can promote fixation of implant 500 to rib 82 while helping to reduce unwanted adherence of soft tissue to outer portion 502A of body 502.

Figure 6:
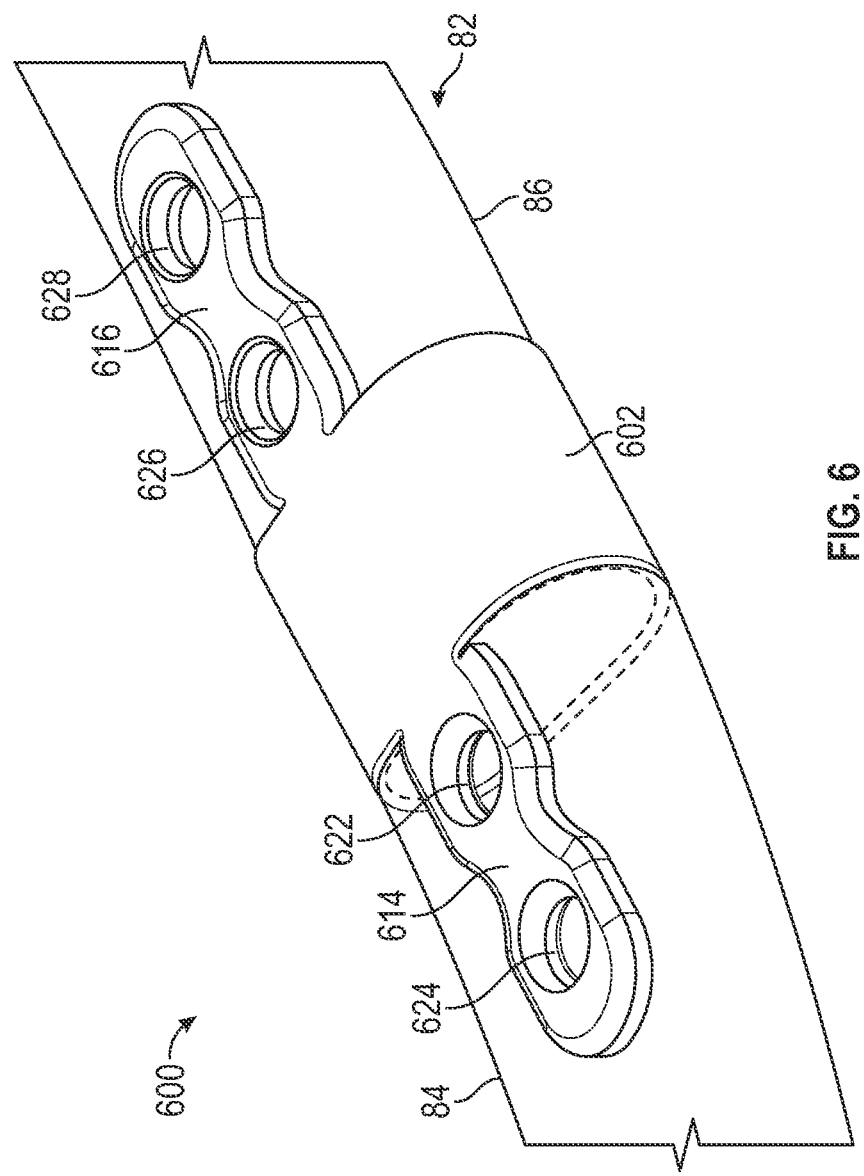
FIG. 6 illustrates an isometric view of a rib implant secured to a rib, in accordance with at least one example of this disclosure.

FIG. 6 illustrates an isometric view of rib implant 600 secured to rib 82, in accordance with at least one example of this disclosure. Rib implant 600 can include plates extending medially and laterally, where the plates engage an outer surface of the rib for affixing the implant to the rib using fasteners. Any of the previously discussed implants can be modified to include plates.

Rib implant 600 can include body 602, medial plate 614 (including bores 622 and 624) and lateral plate 616 (including bores 626 and 628). Rib implant 600 can be similar to rib implant 500, except that rib implant 600 does not include stems.

In operation of some examples, body 602 can be positioned between rib portions 84 and 86 to create a substantially uniform bridge therebetween. In these examples, fasteners can be passed through bores 622, 624, 626, and/or 628 to affix medial plate 614 and lateral plate 616 (and therefore implant 600) to rib portions 84 and 86.

In the example of FIG. 6, body 602 can differ from body 502 in that body 602 can be made of only one material. For example, body 602 can be made of a non-porous material. Using only a single material for body 602 and plates 614 and 616 can help to reduce cost of implant 600.

FIG. 7A illustrates an isometric view of rib implant 700A secured to rib 92, in accordance with at least one example of this disclosure. Rib implant 700A can include a body having a cylindrical shape that can be bent by a surgeon to match a patient's anatomy such as a contour of the rib. Rib implant 700A can also include one or more tapered stems to help ensure engagement between the stem and the intramedullary canal of the rib. Rib implant 700A can also include one or more flanges on either side of the body to help limit translation of rib implant. Any of the previously discussed implants can be modified to include one or more tapered stems, flanges, and/or a body having a cylindrical shape.

Implant 700A can include body 702, medial stem 704, lateral stem 706, medial flange 724, and lateral flange 726. Also shown in FIG. 7A is rib 82, which can include rib portions 84 and 86. Rib portion 84 can include intramedullary canal 84IM and rib portion 86 can include intramedullary canal 86IM. Also shown in FIG. 7A are orientation indicators Medial and Lateral.

Body 702 can be a rigid or semi-rigid member having a substantially cylindrical geometric shape. Body 702 can be comprised of biocompatible materials that are relatively bendable, such as stainless-steel alloys, titanium alloys, and the like.

Medial flange 724 and lateral flange 726 can be flanges or end plates coupled to respective medial and lateral ends of body 702. In some examples, medial flange 724 and lateral flange 726 can be formed of a single piece with body 702 and in other examples, medial flange 724 and lateral flange 726 can be secured to body 702, such as through a welding process. Medial flange 724 and lateral flange 726 can be sized to abut respective rib portions 84 and 86 and to create a substantially uniform transition between medial flange 724 and lateral flange 726 and respective rib portions 84 and 86. In some examples, medial flange 724 and lateral flange 726 can be sized to limit translation of implant 700 relative to rib 82 through contact between medial flange 724 and lateral flange 726 and rib portions 84 and 86, respectively.

Stems 704 and 706 can extend medially and laterally, respectively, from medial flange 724 and lateral flange 726 and can taper as they extend away. In some examples, each of stems 704 and 706 can have multiple tapered portions of varying taper sizes and/or styles including Brown, Morse, Jarno, Jacobs, and the like tapers. In other examples, each of stems 704 and 706 can have a single taper. Each of stems the tapers of stems 704 and 706 can be sized and shaped to engage intramedullary canals 84IM and 861M, respectively, to ensure engagement between stems 704 and 706 and respective intramedullary canals 84IM and 861M. In some examples, each of stems 704 and 706 can be made of a porous or semi-porous material configured to promote ingrowth of rib portions 84 and 86 into stems 704 and 706, respectively. Any of the porous materials discussed above can be used.

In operation of some examples, stem 704 can be inserted into rib portion 84 in a medial direction until flange 714 contacts a lateral end of rib portion 84 and/or until stem 704 contacts an inner width of cortical bone forming intramedullary canal 84IM. Stem 706 can then be inserted into rib portion 86 in a similar manner. As in the examples discussed above, either of stems 704 and 706 can be inserted first and in some examples, stems 704 and 706 can be inserted simultaneously. Either prior to insertion of stems 704 and 706 or after insertion, body 702 can be bent, such as by a surgeon using a bending tool, such as a rod bender. Body 702 can be bent to help match a natural curvature of rib 82, helping to improve respective alignment between stems 704 and 706 and intramedullary canals 84IM and 86IM, which can help improve comfort and can help secure implant 700 to rib 82.

FIG. 7B illustrates an isometric view of a rib implant secured to a rib, in accordance with at least one example of this disclosure. Rib implant 700 can include one or more plates and one or more fasteners extendable through the plates and into the rib. Any of the previously discussed implants can be modified to include one or more plates and/or fasteners.

Implant 700B can include body 702, medial stem 704, lateral stem 706, fasteners 708 and 710, medial plate 714, lateral plate 716, medial flange 724, and lateral flange 726. Also shown in FIG. 7A is rib 82, which can include rib portions 84 and 86. Rib portion 84 can include intramedullary canal 84IM and rib portion 86 can include intramedullary canal 861M. Also shown in FIG. 7B are orientation indicators Medial and Lateral.

Implant 700B can be similar to implant 700A described above with respect to FIG. 7A, except that implant 700B can also include medial and lateral plates 714 and 716 and fasteners 708 and 710. In some examples, medial plate 714 can extend medially from a substantially outer width or outer portion of medial flange 724. Similarly, lateral plate 716 can extend medially from a substantially outer width or outer portion of lateral flange 726. Each of medial and lateral plates 714 and 716 can include bores configured to receive fasteners therethrough. Fasteners 708 and 710 can be secured to medial and lateral plates 714 and 716 and to rib portions 84 and 86 in one or more ways.

As shown in FIG. 7B, fastener 708 can extend through medial plate 714 into rib portion 84. In some examples, fastener 708 can extend through cortical bone of rib portion 84 and into intramedullary canal 841M In other examples, fastener 708 can extend through intramedullary canal 84IM and into cortical bone on the opposite side of intramedullary canal 84IM. In the example of FIG. 7B, fastener 708 can be adjacent to medial stem 704 to help limit translation of implant 700 relative to rib 724. In some examples, a bore in medial plate 714 can guide the placement of fastener 708 relative to medial stem 704.

As also shown in FIG. 7B, fastener 710 can extend through lateral plate 716 (such as through a bore of lateral plate 716) and into lateral stem 706. In some example, fastener 710 can extend through lateral stem 706. In either example, fastener 710 can help secure implant 700B to rib 82.

In some examples, bores in plates 714 and 716 can be recessed (similar to those of implant 600 so that fasteners 708 and 710 can be substantially flush relative to medial and lateral plates 714 and 716 to help reduce palpability of fasteners 708 and 710.

FIG. 8 illustrates an isometric view of rib implant 800 secured to rib 92, in accordance with at least one example of this disclosure. The example of FIG. 8 can be similar to those discussed above where implant 800 is secureable to rib 92, except that implant 800 is a multi-piece assembly. Implant 800 can include stem 802, stem 804, and coupler 806. Also shown in FIG. 8 is rib 92 having rib portions 94 and 96. Also shown in FIG. 8 are orientation indicators Medial and Lateral.

Each of stems 802 and 804 can be rigid or semi-rigid members comprised of biocompatible materials. In some examples, each of stems 802 and 804 can include a portion insertable into a rib portion, where the insertable portion can be made of a porous or semi-porous material configured to promote bone ingrowth. Each of stems 802 and 804 can be similarly sized (or can be of different sizes in some examples) and can be sized and shaped for engagement with coupler 806. Coupler 806 can be a rigid or semi-rigid member configured to receive each of stems 802 and 804 therein and configured to secure each of stems 802 and 804 thereto such as through a clamping, threaded, or locking mechanism. In some examples, coupler 806 can slide over one or more of stems 802 and 804 for positioning of coupler 806.

The multi-piece assembly of implant 800 can allow for individual insertion of stems 802 and 804 where a small gap (or fracture) between rib portions 94 and 96 is desired (or exists) and a single piece implant is difficult to secure within intramedullary canals of rib portions 94 and 96.

FIG. 9 illustrates an isometric view of rib implant 900 secured to rib 92, in accordance with at least one example of this disclosure. The example of FIG. 9 can be similar to the example of FIG. 8 discussed above, such that the member coupling the multi-piece assembly of implant 900 is a fastener, such as a screw or bolt.

Implant 900 can include medial stem 902, lateral stem 904, and coupler 906. Medial stem 902 can include female end 908 and bore 910. Lateral stem 904 can include male end 912 and bore 914.

Each of stems 902 and 904 can be similar to those discussed above, except that medial stem 902 can include female end 908 located at a lateral portion of medial stem 902, where female end 908 can be configured to receive male end 912 of lateral stem 904 therein to secure lateral stem 904 within medial stem 902. Once lateral stem 904 is inserted into medial stem 902, fastener 906 can be passed through bore 910 of medial stem 902 and bore 914 of lateral stem 904 to further secure medial stem 902 and lateral stem 904. In some examples, fastener 906 can be excluded, such as where male end 912 and female end 908 engage in a threaded (or otherwise locking) fashion.

The multi-piece assembly of implant 900 can allow for insertion of stems 902 and 904 where a small gap (or fracture) between rib portions 94 and 96 is desired (or exists) and a single piece implant is difficult to secure within intramedullary canals of rib portions 94 and 96.

Figure 10:
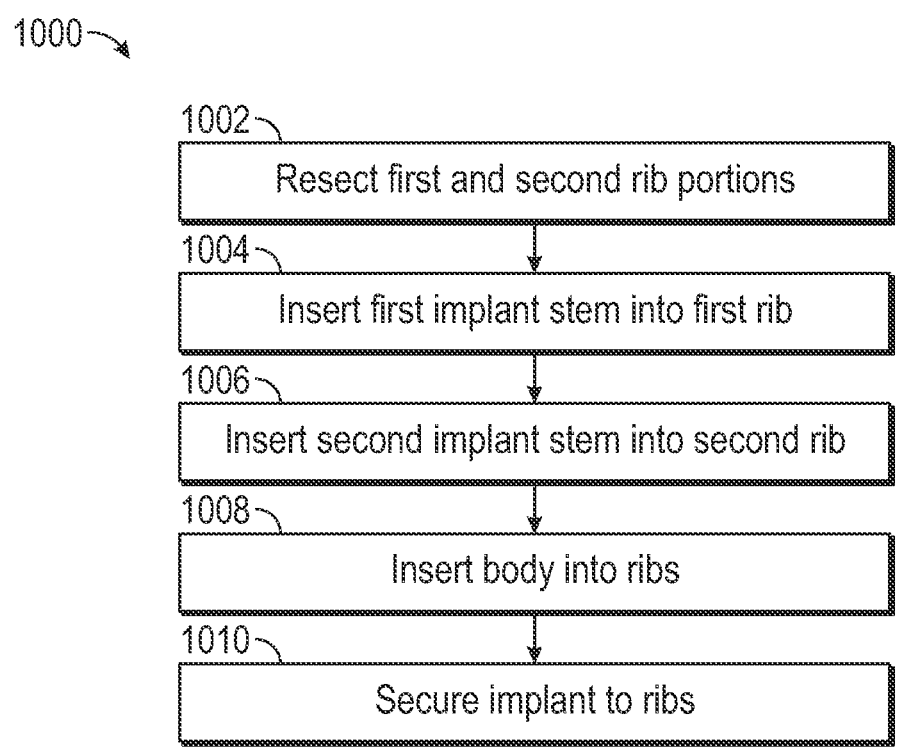
FIG. 10 illustrates a schematic of a method, in accordance with at least one example of this disclosure.

FIG. 10 illustrates a schematic of method 1000, in accordance with at least one example of this disclosure. Method 1000 can be a method of securing an implant to a rib of a patient. The steps or operations of method 1000 are illustrated in a particular order for convenience and clarity; many of the discussed operations can be performed in a different sequence or in parallel without materially impacting other operations. Method 1000 as discussed includes operations performed by multiple different actors, devices, and/or systems. It is understood that subsets of the operations discussed in method 1000 attributable to a single actor, device, or system could be considered a separate standalone process or method.

Method 1000 can begin at step 1002 where rib portions can be resected, such as rib portions 74 and 76 of FIGS. 4A-4F. In some examples, a resection may not be performed, such as with the steps shown in FIGS. 3A-3C. At step 1004, a first stem can be inserted into a first rib portion. For example, stem 104 can be inserted into rib portion 54, as shown in FIG. 2. At step 1006, a second stem can be inserted into a second rib portion. For example, stem 106 can be inserted into rib portion 56, as shown in FIG. 2.

At step 1008, a body of the implant can be inserted into the ribs. For example, body 302 can be inserted into rib portions 64 and 66. In some examples where the body does abut the rib portions (as shown in FIG. 2), step 1008 may not be performed. At step 1010 the implant can be secured to the ribs. For example, fasteners 408 and 410 can be secured to rib portions 74 and 76 and medial and lateral stems 404 and 406 to secure implant 400 to rib 72.

EXAMPLES

The following, non-limiting examples, detail certain aspects of the present subject matter to solve the challenges and provide the benefits discussed herein, among others.

Example 1 is a rib implant securable to first and second rib portions of a rib, the rib implant comprising: a body the body including a first end and an opposite second end, the body configured to span a first rib portion of a rib at the first end and a second rib portion of the rib at the second end; a first porous stem extending from the first end of the body, the first porous stem insertable into a first intramedullary canal of the first rib portion; and a second porous stem extending from the second end of the body opposite the first porous stem, the second porous stem insertable into a second intramedullary canal of the second rib portion to secure, together with the first porous stem, the first rib portion and the second rib portion.

In Example 2, the subject matter of Example 1 optionally includes wherein the body is comprised of a porous material configured to promote bone ingrowth.

In Example 3, the subject matter of any one or more of Examples 1-2 optionally include wherein the body is comprised of a resorbable material.

In Example 4, the subject matter of any one or more of Examples 1-3 optionally include wherein one or more of the body, the first porous stem, and the second porous stem is comprised of Lactosorb.

In Example 5, the subject matter of any one or more of Examples 1-4 optionally include wherein the first porous stem is comprised of a porous material configured to promote bone ingrowth.

In Example 6, the subject matter of any one or more of Examples 1-5 optionally include wherein one or more of the body, the first porous stem, and the second porous stem is comprised of a material selected from a group consisting of Trabecular metal, Regenerex, and OsseoTi.

In Example 7, the subject matter of any one or more of Examples 1-6 optionally include wherein the body is comprised of a solid material and is sized and shaped to match a size and a shape of each of the first rib portion and the second rib portion to create a substantially uniform bridge between the first rib portion and the second rib portion.

In Example 8, the subject matter of any one or more of Examples 1-7 optionally include wherein the first porous stem is configured to create an interference fit with the first intramedullary canal.

In Example 9, the subject matter of any one or more of Examples 1-8 optionally include a fastener extendable through the first stem to secure the first stem to the first rib portion.

In Example 10, the subject matter of any one or more of Examples 1-9 optionally include a plate extending from the body substantially parallel to the first stem, the plate configured to engage a face of the first rib portion.

In Example 11, the subject matter of Example 10 optionally includes wherein the plate includes a plate bore and the first stem includes a stem bore substantially coaxial with the plate bore.

In Example 12, the subject matter of any one or more of Examples 1-11 optionally include a fastener extendable through the plate bore and the stem bore to secure the first stem and the plate to the first rib portion.

In Example 13, the subject matter of anyone or more of Examples 1-12 optionally include wherein the body comprises a substantially cylindrical rod.

In Example 14, the subject matter of Example 13 optionally includes wherein the rod is bendable to match a curvature of a rib of a patient.

In Example 15, the subject matter of any one or more of Examples 13-14 optionally include a flange secured to the body between the body and the first stem.

In Example 16, the subject matter of any one or more of Examples 13-15 optionally include wherein at least one of the first stem and second stem comprises a tapered extension.

Example 17 is a rib implant system comprising: an implant securable to a first rib portion of a rib and a second rib portion of the rib, the implant comprising: a body the body including a first end and an opposite second end, the body configured to span a first rib portion of a rib at the first end and a second rib portion of the rib at the second end; a first porous stem extending from the first end of the body, the first porous stem insertable into a first intramedullary canal of the first rib portion; and a second porous stem extending from the second end of the body opposite the first porous stem, the second porous stem insertable into a second intramedullary canal of the second rib portion to secure, together with the first porous stem, the first rib portion and the second rib portion.

In Example 18, the subject matter of Example 17 optionally includes a cut guide configured to guide resection of the first rib portion and the second rib portion so that the rib implant is positionable therebetween.

In Example 19, the subject matter of any one or more of Examples 17-18 optionally include a fastener securable to the first rib portion and the first stem to secure the rib implant to the first rib portion.

Example 20 is a rib implant securable to a medial rib portion of a rib and a lateral rib portion of the rib, the rib implant comprising: a first porous stem including a medial portion and a lateral portion, the medial portion insertable into a first intramedullary canal of the medial rib portion; and a second porous stem including a medial portion and a lateral portion, the lateral portion insertable into a lateral intramedullary canal of the lateral rib portion, the lateral portion of the first porous stem securable to the medial portion of the second porous stem to secure the medial rib portion and the lateral rib portion.

In Example 21, the subject matter of Example 20 optionally includes wherein the medial portion of the second porous stem is insertable into the lateral portion of the first porous stem.

In Example 22, the subject matter of any one or more of Examples 20-21 optionally include a coupler securable to the medial portion of the second porous and the lateral portion of the first porous stem.

In Example 23, the system, device, or method of anyone of or any combination of Examples 1-22 is optionally configured such that all elements or options recited are available to use or select from.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. A rib implant securable to first and second rib portions of a rib, the rib implant comprising:
 a body including a first end portion and an opposite second end portion, the body configured to span a first rib portion of a rib at the first end portion and a second rib portion of the rib at the second end portion;
 a first stem extending from and extending beyond the first end portion of the body, the first stem being tapered and insertable into a first intramedullary canal of the first rib portion;
 a second stem extending from and extending beyond the second end portion of the body opposite the first stem, the second stem being tapered and insertable into a second intramedullary canal of the second rib portion to secure, together with the first stem, the first rib portion and the second rib portion; and
 a plate extending from the first end portion substantially parallel to the first stem and extending beyond the body, the plate configured to engage a face of the first rib portion when the first stem is inserted into the first intramedullary canal of the first rib portion.

2. The rib implant of claim 1, wherein the plate includes a plate bore and the first stem includes a stem bore substantially coaxial with the plate bore.

3. The rib implant of claim 2, further comprising:
a fastener extendable through the plate bore and the stem bore to secure the first stem and the plate to the first rib portion.

4. The rib implant of claim 2, further comprising:
a second plate extending from the second end portion of the body substantially parallel to the second stem, the second plate configured to engage a face of the second rib portion.

5. The rib implant of claim 4, wherein the second plate includes a second plate bore and the second stem includes a second stem bore substantially coaxial with the second plate bore.

6. The rib implant of claim 1, wherein the plate extends laterally beyond the first stem.

7. A rib implant securable to first and second rib portions of a rib, the rib implant comprising:
a body including a first end portion and an opposite second end portion, the body configured to span a first rib portion of a rib at the first end portion and a second rib portion of the rib at the second end portion;
a first stem extending from the first end portion of the body, the first stem insertable into a first intramedullary canal of the first rib portion;
a second stem extending from the second end portion of the body opposite the first stem, the second stem insertable into a second intramedullary canal of the second rib portion to secure, together with the first stem, the first rib portion and the second rib portion;
a first plate extending from the first end portion substantially parallel to the first stem, the first plate configured to engage a face of the first rib portion when the first stem is inserted into the first intramedullary canal of the first rib portion;
a second plate extending from the second end portion substantially parallel to the second stem, the second plate configured to engage a face of the second rib portion when the second stem is inserted into the intramedullary canal of the second rib portion;
a first flange connected between the body and the first stem, the first flange engageable with the first rib portion; and
a second flange connected between the body and the second stem, the second flange engageable with the second rib portion.

8. The rib implant of claim 7, wherein the first plate includes a first plate bore and the first stem includes a first stem bore substantially coaxial with the first plate bore.

9. The rib implant of claim 8, wherein the second plate includes a second plate bore and the second stem includes a second stem bore substantially coaxial with the second plate bore.

10. The rib implant of claim 9, further comprising:
a first fastener extendable through the first plate bore and the first stem bore to secure the first stem and the first plate to the first rib portion; and
a second fastener extendable through the second plate bore and the second stem bore to secure the second stem and the second plate to the second rib portion.

11. The rib implant of claim 7, wherein the first plate extends from an outer portion of the first flange away from the second flange, and wherein the second plate extends from an outer portion of the second flange away from the first flange.

* * * * *